(12) United States Patent
Peng et al.

(10) Patent No.: US 7,303,559 B2
(45) Date of Patent: Dec. 4, 2007

(54) MULTIPLEFUNCTION SURGICAL DISSECTOR

(76) Inventors: Shuyou Peng, Room 301, House 10, Chaohui Xin cun, Hangzhou (CN); Ying Su, Room 201, House 1, Xincheng Fang, Binjiang District, No. 4, Hangzhou (CN)

( * ) Notice: Subject to any disclaimer, the term of this patent is extended or adjusted under 35 U.S.C. 154(b) by 123 days.

(21) Appl. No.: 10/409,461

(22) Filed: Apr. 8, 2003

(65) Prior Publication Data

US 2004/0162553 A1 Aug. 19, 2004

(30) Foreign Application Priority Data

Feb. 19, 2003 (CN) .............................. 03 1 15446

(51) Int. Cl.
*A61B 18/14* (2006.01)
(52) U.S. Cl. .......................... 606/41; 606/45
(58) Field of Classification Search .................. 606/41, 606/45, 47; 607/96, 98
See application file for complete search history.

(56) References Cited

U.S. PATENT DOCUMENTS

| 5,071,418 | A |   | 12/1991 | Rosenbaum |         |
|-----------|---|---|---------|-----------|---------|
| 5,154,709 | A |   | 10/1992 | Johnson   |         |
| 5,242,442 | A | * | 9/1993  | Hirschfeld | 606/42 |
| 5,246,440 | A |   | 9/1993  | Van Noord |         |
| 5,254,117 | A |   | 10/1993 | Rigby et al. |      |
| 5,318,565 | A |   | 6/1994  | Kuriloff et al. |   |
| 5,413,575 | A |   | 5/1995  | Haenggi   |         |
| 5,496,314 | A | * | 3/1996  | Eggers    | 606/41  |
| 5,797,907 | A | * | 8/1998  | Clement   | 606/49  |
| 5,810,809 | A |   | 9/1998  | Rydell    |         |
| 5,836,909 | A |   | 11/1998 | Cosmescu  |         |
| 6,245,070 | B1 | * | 6/2001 | Marquis et al. | 606/51 |
| 6,293,945 | B1 | * | 9/2001 | Parins et al. | 606/45 |
| 6,375,651 | B2 | * | 4/2002 | Grasso et al. | 606/15 |
| 6,428,539 | B1 | * | 8/2002 | Baxter et al. | 606/49 |
| 6,669,695 | B2 | * | 12/2003 | Luigi     | 606/49  |
| 6,702,812 | B2 | * | 3/2004 | Cosmescu  | 606/41  |
| 7,169,148 | B2 | * | 1/2007 | O'Halloran | 606/49 |
| 2002/0099373 | A1 |  | 7/2002 | Schulze et al. | |

FOREIGN PATENT DOCUMENTS

WO  WO 00/28908  5/2000

* cited by examiner

*Primary Examiner*—Michael Peffley
*Assistant Examiner*—Aaron Roane
(74) *Attorney, Agent, or Firm*—Dorsey & Whitney LLP

(57) ABSTRACT

The present invention provides A surgical dissector, comprising: a housing having a first end and a second end, and on the first end is formed a suction inlet; a circuit board disposed within the housing; a first switch connected to the circuit board for performing function of electrical coagulating, and disposed on the housing; a second switch connected to the circuit board for performing function of electrical cutting, and disposed on the housing; a tube disposed in the housing and extended out of the second end of the housing, the extended end of the tube having a means for performing suction and/or blunt dissectingion and/or scraping and/or push peeling at the situs of operation; an electrosurgical knife disposed in the housing and extended out of the second end of the housing, the electrosurgical knife being connected electrically to the circuit board, and having the functions of electrical coagulating and cutting; and a retractable means for relative retractable movement between the tube and the electrosurgical knife. By means of the surgical dissector of the present invention, additional actions of blunt dissecting, scraping and push peeling are provided. Moreover, surgical dissector of the present invention can rotate by a certain angle at will, conforming to different habit of operation.

15 Claims, 6 Drawing Sheets

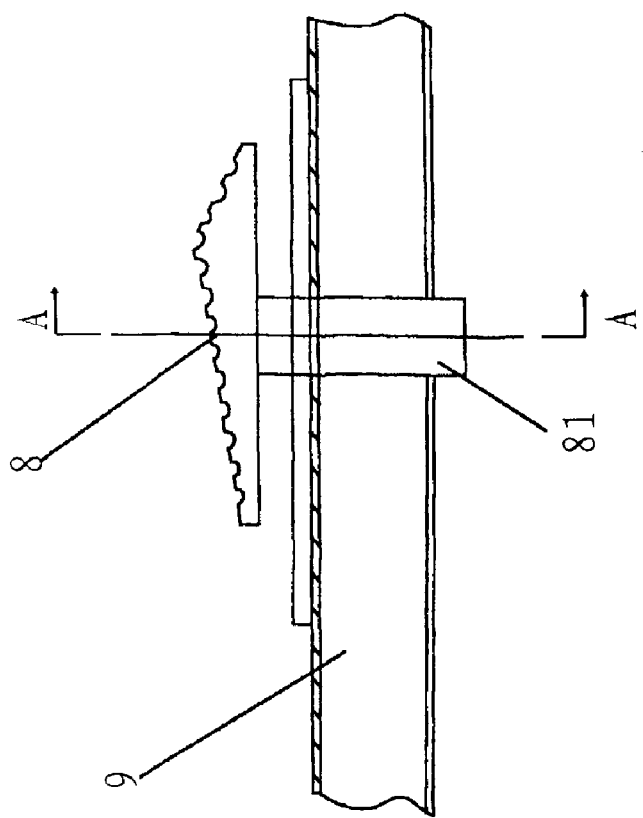
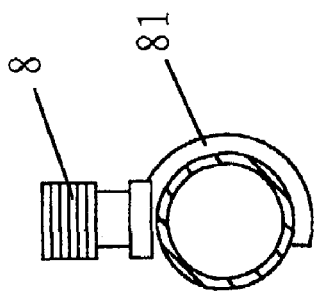

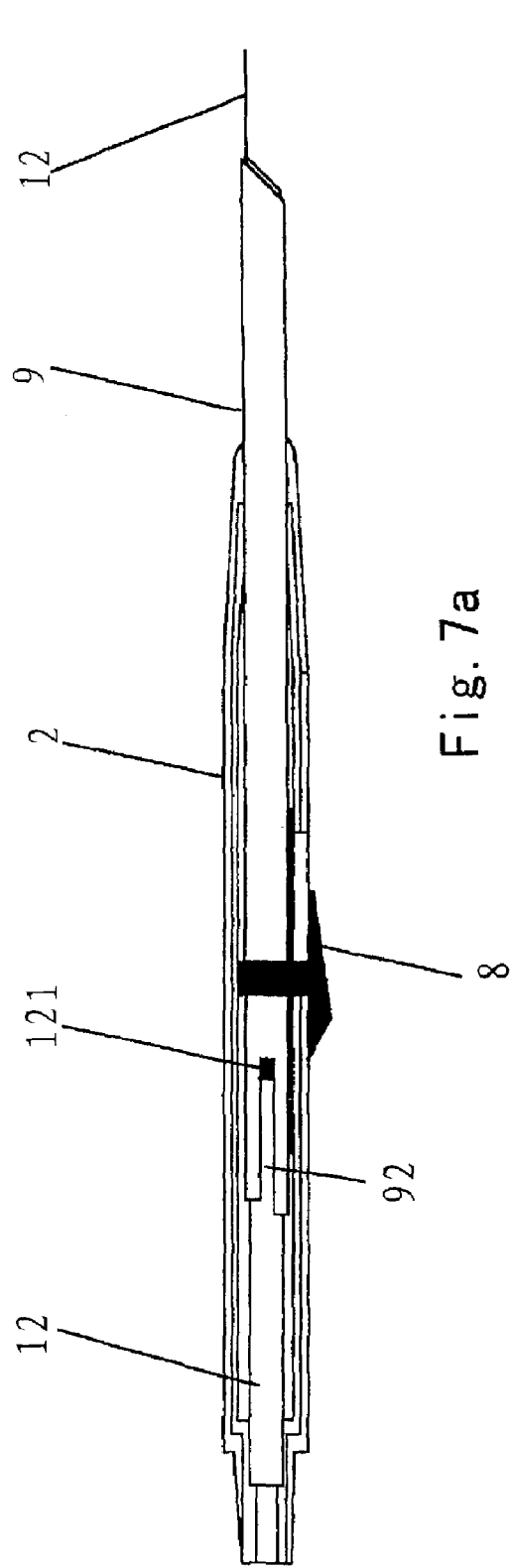
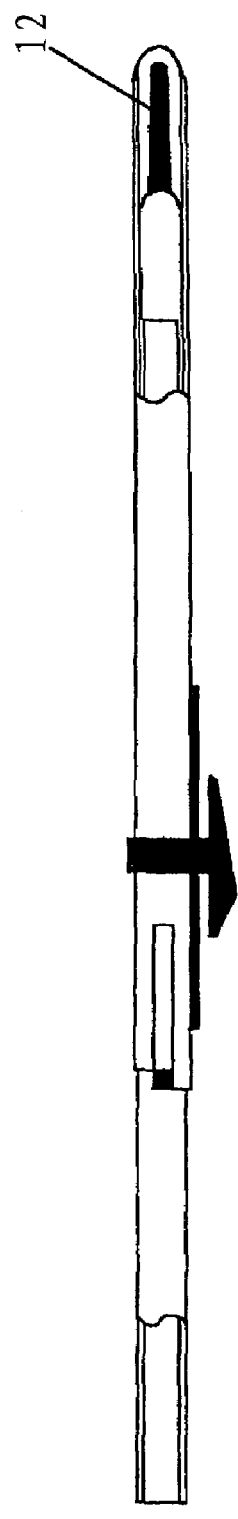

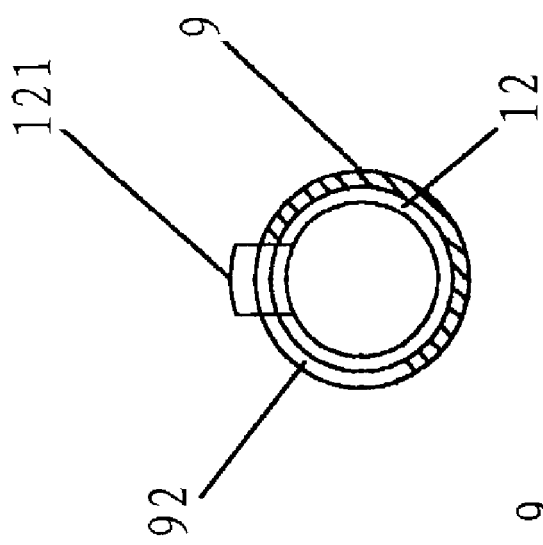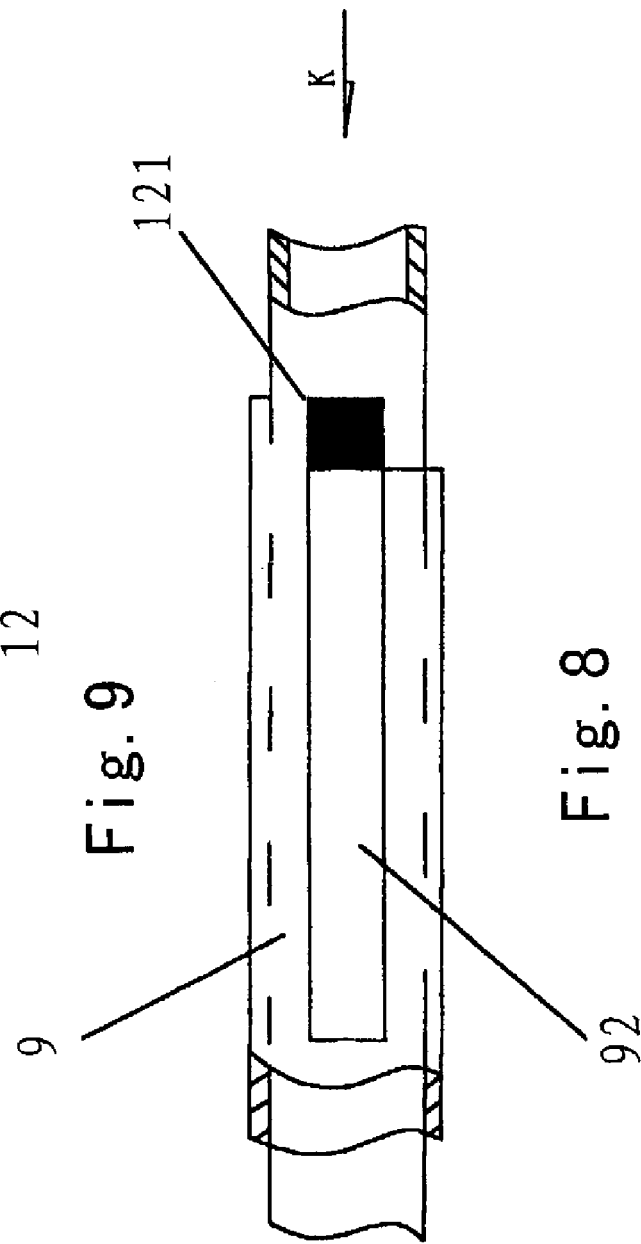

US 7,303,559 B2

MULTIPLEFUNCTION SURGICAL DISSECTOR

CROSS-REFERENCE TO RELATED APPLICATIONS

This application claims priority to Chinese Patent Application 03115446.8, filed on Feb. 19, 2003, the contents of which are hereby incorporated by reference.

FIELD OF THE INVENTION

The present invention generally relates to surgical instruments, particularly to a dissector for surgical operation.

BACKGROUND OF THE INVENTION

Electrosurgical knife is an important instrument for electrically cutting and coagulating, which is widely used in surgical operation. In comparison with traditional surgical knife, the electrosurgical knife has the advantage of less blood loss and higher efficiency, and becomes an indispensable instrument for most surgeons. However, during the procedures of dissection (electrical cutting) and/or blood coagulation (electrical coagulation) by means of electrosurgical knife, smokes are generally generated, impairing the field of vision of the surgeon. In addition, blood and debris produced during surgical operation also obstruct the operation. For removing the smokes, blood and debris, a suction device is necessary to follow the movement of the knife synchronously.

Originally, the electrosurgical knife and the suction device are separated from each other, but in this way, both hands of a surgeon are occupied. Alternatively, two practitioners are needed for operation, causing much troubles in surgery operation. Moreover, application of separate suction device brings difficulties in precise positioning of surgical operation. Consequently, dissectors having both the electrosurgical knife and the suction device and thereby having functions of cutting, suction and coagulation simultaneously, was provided, for example, in U.S. Pat. Nos. 5,071,418, 5,246,440, 5,318,565 and 5,413,575.

Although different surgical dissectors have been disclosed in the above-said U.S. patents, all of them have the disadvantages of complication, bulk and inconvenience. It is important that each of these dissectors comprise a knife portion and a suction portion, with the knife portion performing electrical cutting and coagulating, and the suction portion performing suction. In this way, the functions of electrosurgical knife and suction device are rather limited, and the suction device can not be utilized efficiently.

SUMMARY OF THE INVENTION

To overcome the above-said shortcomings, the present invention aims to provide a multifunction surgical dissector, not only simple in structure and convenient in use, but also capable of performing electrical cutting, electrical coagulating, and suctioning simultaneously.

Another object of the present invention is to provide a multifunction dissector capable of blunt dissecting, scraping and push peeling.

Yet another object of the present invention is to provide a multifunction dissector capable of rotating easily and meeting different requirements of use.

To realize the above said objects, the present application provides a surgical dissector, comprising: a housing having a first end and a second end, and on the first end is formed a suction inlet; a circuit board disposed within the housing; a first switch connected to the circuit board for performing function of electrical coagulating, and disposed on the housing; a second switch connected to the circuit board for performing function of electrical cutting, and disposed on the housing; a tube disposed in the housing and extended out of the second end of the housing, the extended end of the tube having a means for performing suction and/or blunt dissectingion and/or scraping and/or push peeling at the situs of operation; an electrosurgical knife disposed in the housing and extended out of the second end of the housing, the electrosurgical knife being connected electrically to the circuit board, and having the functions of electrical coagulating and cutting; and a retractable means for relative retractable movement between the tube and the electrosurgical knife.

The surgical dissector according to the present application is simple in structure, and convenient for use. By means of the surgical dissector of the present invention, additional actions of blunt dissecting, scraping and push peeling are provided. Moreover, surgical dissector of the present invention can rotate by a certain angle at will, conforming to different habit of operation.

DESCRIPTION OF THE DRAWINGS

FIG. 3 is an enlarged partial view of a slide switch and its surrounding structure;

FIG. 4 is a cross-sectional view taken along line 4-4 of FIG. 3;

FIG. 7a is a front cross-sectional view of the surgical dissector of another embodiment according to the present invention, in which the electrosurgical knife is exposed;

FIG. 7b is a top cross-sectional view of the said dissector, in which the electrosurgical knife is covered by an extended multipurpose tube;

FIG. 8 is a partial view of a positioning structure of the multipurpose tube of the dissector;

FIG. 9 is a view from the arrow K in FIG. 8.

DETAILED DESCRIPTION OF PREFERRED EMBODIMENT

Figure 1:
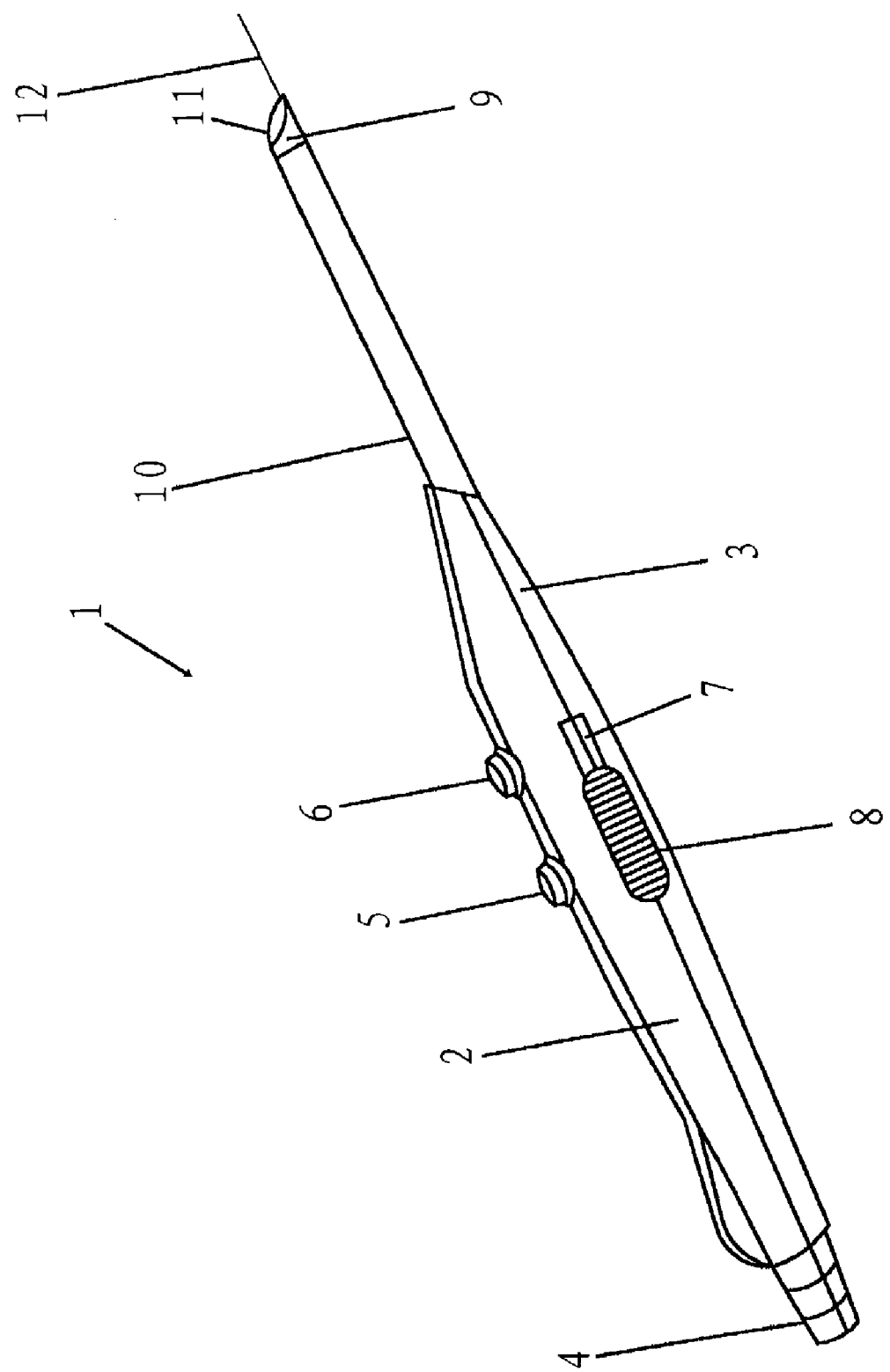
FIG. 1 is a perspective view of a surgical dissector according to an embodiment of the present invention.

Referring to FIG. 1, according to a preferred embodiment of the present invention, a surgical dissector 1 comprises an elongated housing composed of an upper section 2 and a lower section 3. At one end of the housing, a suction inlet 4 is formed for connecting to a suction hose (not shown), which is connected to a vacuum suction source. On one side of the housing, a push button 5 for electrical coagulating and a push button 6 for electrical cutting are provided, so as to be switched between coagulating and cutting. On another side of the housing, a sliding slot 7 is formed, in which a slide switch 8 is slidably accommodated. A metallic multipurpose tube 9 is disposed in the housing, with one end connected to the suction inlet 4, and another end extending out of another end of the housing. The end 11 of the multipurpose tube 9 is beveled with a sharp angle of about 45° with respect to the axis of the tube. Said "multipurpose tube" is a tube having not only the function of suction, but also the functions of electrical coagulating and cutting. Here, the action of electrical cutting is different from the ordinary cutting, it utilizes the beveled end 11 to perform blunt dissecting, scraping and push peeling, capable of playing an important role in surgeries. For the sake of safety, the periphery surface of the multipurpose tube 9 is covered with, for example, an insulation tube 10 made of plastics. An electrosurgical knife 12 made of metal is disposed retractably in the multipurpose tube 9, the retractable structure of which will be described in detail hereinafter. In this embodiment, the head of the electrosurgical knife 12 is in a shape of blade, and the remaining part of the knife is also tubular in shape, and is in electrically conductive contact with the multipurpose tube 9. The remaining part of the knife forms a passageway for suction. If desired, the electrosurgical knife, as a whole, can be made in a blade shape. In this situation, the multipurpose tube 9 will directly function as the passageway of suction. To prevent from accumulation of char and tissue coagulum, the multipurpose tube 9 and the electrosurgical knife 12 may be coated with a stick-proof material, such as polytetrafluoroethylene. In addition, a cleaning rod (not shown) can be provided for elimination of blocking and prevention of sticking.

Figures 2A, 2B:
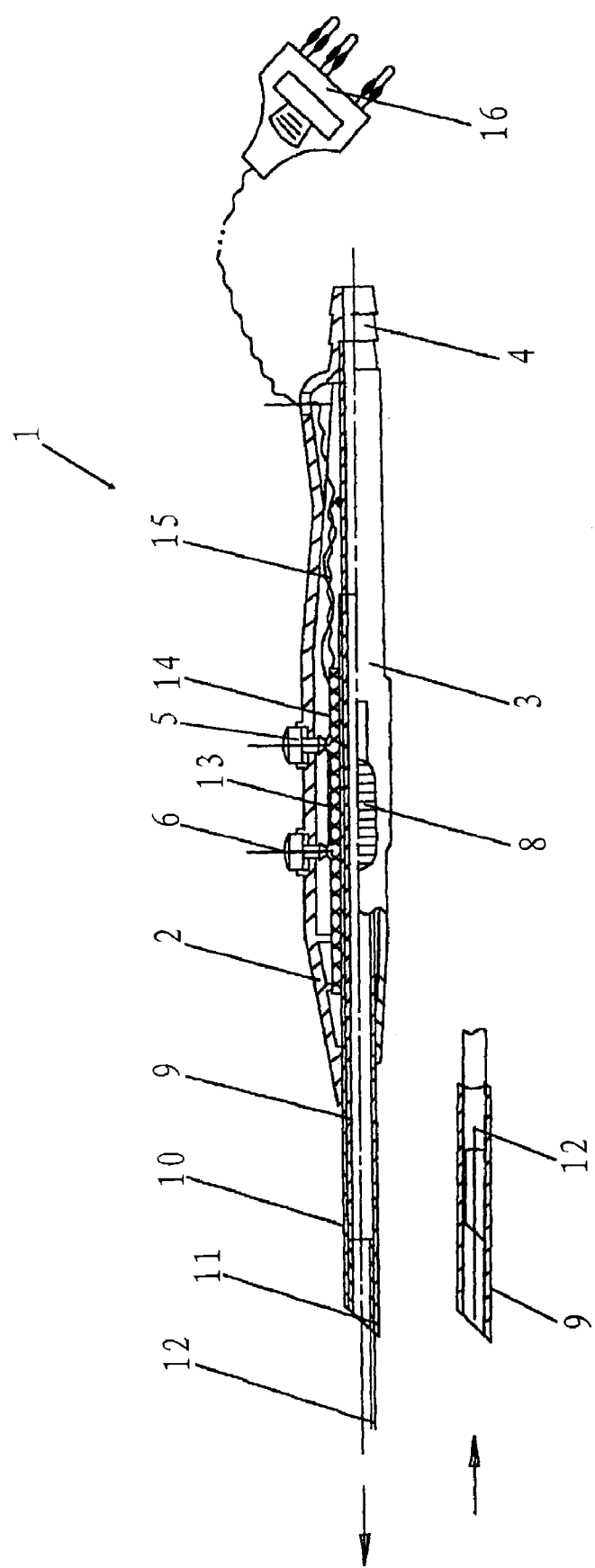
FIG. 2a is a partial longitudinal cross-sectional view of the dissector.
FIG. 2b is a partial view of the dissector with a retracted knife.

FIG. 2a shows in detail the interior structure of the surgical dissector 1. As shown in the figure, the push button 5 for electrical coagulating and the push button 6 for electrical cutting act on a circuit board 14 through a spring leaf 13. The circuit board 14 is connected electrically to the electrosurgical knife 12 through wires 15, and connected electrically to a high frequency source (not shown) through wires and a plug 16. The electrosurgical knife 12 and the multipurpose tube 9 can move with respect to each other. FIG. 2a shows the electrosurgical knife 12 in a state of relatively extending out of the tube, and FIG. 2b. shows a state of relatively retracting into the tube. It is important that the electrosurgical knife 12 is in electrically conductive contact with the multipurpose tube 9, thereby enabling the multipurpose tube 9 to have the function of electrical coagulating and electrical cutting. Hence, during the surgical procedure, in addition to using the multipurpose tube 9 as a continuous suction device, the tip portion of the end 11 can discharge and perform electrical coagulating and cutting, and the beveled plane can perform scraping and push peeling. With these functions of the multipurpose tube 9, a novel "scrape and suction" method of surgical procedure is created, which is particularly adapted to general surgery, such as for liver, gall and pancreas.

FIG. 3 and FIG. 4 illustrate the slide switch 8 and its surrounding structure. The slide switch 8 comprises a substantially semicircular hoop 81, which is disposed around the multipurpose tube 9 for moving the tube forward or backward. It should be noted that the multipurpose tube 9 is stationary with respect to the slide switch 8 in longitudinal direction, but it can rotate in circumferential direction, which is another novel feature of the present invention. On account of that the multipurpose tube 9 can rotate, the user may make the beveled plane of the end 11 in different orientation at his/her will, thereby convenient for performing suction, electrical cutting and coagulating at different situs. Moreover, while grasping the dissector 1, different surgeons can have different habit, for example, some practitioners like to press push buttons for electrical coagulating or cutting with thumb, while others like to press with forefinger. On account of that the multipurpose tube 9 is capable of rotating to any orientation, it can meet the requirements of different surgeons. For the relative positioning of the multipurpose tube 9, a groove (not shown) is provided on the insulation tube by removing a part of the insulation tube 10. The slide switch 8 is fitted in the groove. Rotation of the multipurpose tube 9 relative to the slide switch 8 can be held in place by means of friction or by positioning device to be described hereinafter.

Figure 6:
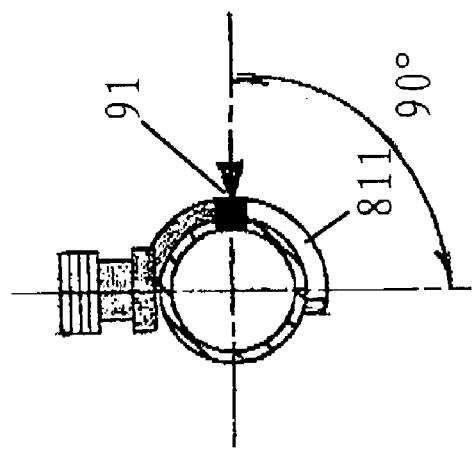
FIG. 6 is a cross-sectional view taken along line 6-6 of FIG. 5.
Figure 5:
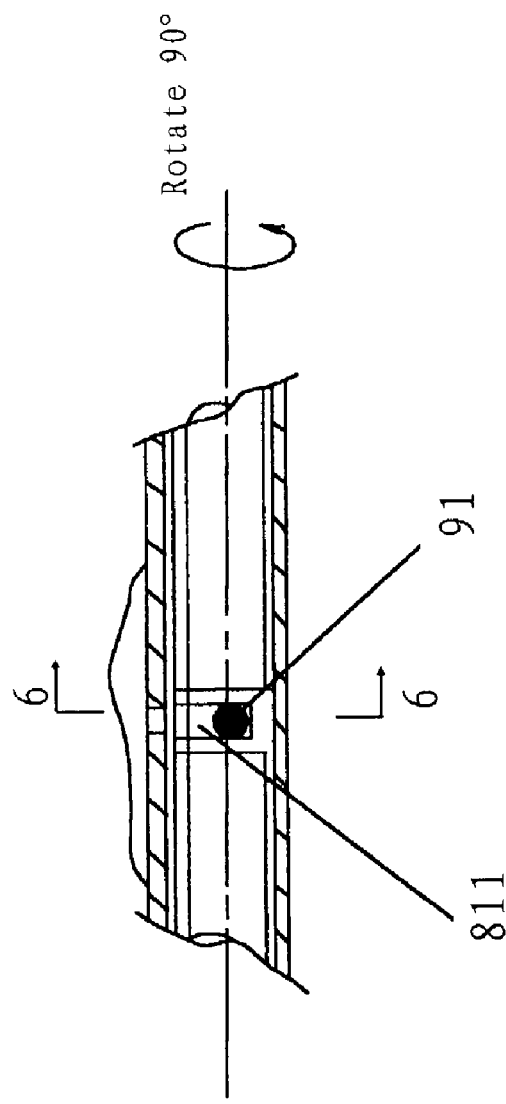
FIG. 5 is an enlarged partial view of a slide switch and its surrounding structure of another embodiment.

FIG. 5 and FIG. 6 illustrate a positioning device for the multipurpose tube 9. As shown in the figures, a recess 811 is circumferentially disposed in the hoop 81, and a stopping projection 91 formed by means of, for example, welding or punching, is disposed on the multipurpose tube 9. The depth of the recess 811 can be changed according to different requirements. Usually, the depth equals to about ¼ of the length of circumference. Thus, when the multipurpose tube 9 rotates about 90°, stopping projection 91 will abut against the bottom of the slot 811, so that the multipurpose tube 9 cannot rotate further.

FIG. 7a and FIG. 7b illustrate a surgical dissector according to another embodiment, which is provided with another positioning device. As shown, at the end of the multipurpose tube 9, an L-shaped slot 92 is formed, and a stopping projection 121 is disposed on the electrosurgical knife 12. The depth of the L-shaped slot 92 equals to about the stroke of the slide switch 8. As shown in FIG. 7a, when the slide switch 8 arrives at the upper stop point, stopping projection 121 will abut against the bottom of the slot 92, and the multipurpose tube 9 will retract completely, so that the electrosurgical knife 12 is exposed completely. As shown in FIG. 7b, when the slide switch 8 arrives at the lower stop point, the multipurpose tube 9 is exposed completely, and the electrosurgical knife is in a retracted state. At that time, the stopping projection 121 arrives at the turn point (the intersection of the longitudinal side and the lateral side of the letter "L") of the L-shaped slot 92. In this state, multipurpose tube 9 can be rotated, until the stopping projection comes into contact with the end of the lateral side of the "L". The rotating angle of the multipurpose tube 9 can also be set up according to different requirements, that is, it can be realized by simply setting up a suitable length of the lateral side of the L-shape in slot 92. In this embodiment, the length of the lateral side of the L-shape is set up to be about ¼ of the circumference, so that the angle of the rotation of the multipurpose tube 9 is about 90°.

FIG. 8 and FIG. 9 illustrate more clearly in detail about the above-said positioning structure. In FIG. 8, sopping projection 121 arrives at the intersection of the longitudinal side and the lateral side of the L-shape slot 92, and at this position multipurpose tube 9 can be rotated to reach different angles. FIG. 9 is a view from arrow K in FIG. 8, wherein the engagement of the stopping projection 121 and the slot 92 is clearly shown.

How to use the multifunction surgical dissector of the present invention is to be described as follows.

During the surgical procedure, surgeons could switch over between the electrosurgical knife 12 and the multipurpose tube 9 by means of slide switch 8 according to the requirements of operation. While performing the sharp dissection, slide switch is pulled backward, and the electrosurgical knife is exposed for electrical coagulating and cutting. At the same time, multipurpose tube 9 can be used for suction through the vacuum suction source, thereby removing the blood, debris and smoke generated during the surgical procedure. While performing the blunt dissectingion, scraping or push peeling, slide switch 8 is pushed forward, and the electrosurgical knife 12 is covered by the multipurpose tube 9, so that the tip portion of the multipurpose tube 9 can be used for electrical coagulating and cutting, and the beveled plane of the tube 9 can be used for scraping and push peeling. At the same time, the multipurpose tube 9 can still perform suctioning to remove the blood, debris and smoke generated during the surgical procedure. In addition, if desired, the multipurpose tube 9 can be rotated by a certain angle to meet different requirements of operation, or to conform to different habit of use.

Moreover, to prevent from accumulation of char and tissue coagulum, the multipurpose tube 9 can be made of nontoxic plastic material (for example, ABS or polypropylene). Since the multipurpose tube 9 is then not electrically conductive, it has no longer functions of electrical coagulating and cutting. Nevertheless, in practical operation, the dissector can also perform electrical coagulating and cutting by slightly extending the electrosurgical knife out of the multipurpose tube 9.

While this invention has been described through the illustration of several preferred embodiments, it will be obvious to those skilled in the art that equivalent changes and modifications on the basis of above description can be made without departure from scope of protection of the present invention. Specifically, different from the above-said embodiments, the electrosurgical knife 12 could be disposed out of the multipurpose tube 9, and the slide switch 8 is attached to the electrosurgical knife 12, making the knife 12 retractable. Besides, the electrosurgical knife 12 and the multipurpose tube 9 can be disposed side by side, and the slide switch is attached to either of the two portions, making them retractable relatively. Moreover, the electrosurgical knife can also be rotary to meet different requirements of users. This feature can be fulfilled by providing the similar rotating and positioning device as the above-said. Consequently, the scope of protection of the present invention is limited only by the appended claims and not by the particular description above.

What is claimed is:

1. A surgical dissector, comprising:
    a housing having a first end and a second end, and on the first end is formed a suction inlet;
    a circuit board disposed within the housing;
    a first switch connected to the circuit board for performing function of electrical coagulating, and disposed on the housing;
    a second switch connected to the circuit board for performing function of electrical cutting, and disposed on the housing;
    a multipurpose tube, having a suction passageway, disposed in the housing and extended out of the second end of the housing, and having a beveled end with an inclined plane, the multipurpose tube dissecting and simultaneously performing suction at situ of operation, the multipurpose tube scraping and simultaneously performing suction at situ of operation, and the multipurpose tube push peeling and simultaneously performing suction at situ of operation;
    an electrosurgical knife, having a suction passageway, disposed in the housing and extended out of the second end of the housing, the electrosurgical knife being connected electrically to the circuit board, and having the functions of electrical coagulating and cutting; and
    a retractable means for relative retractable movement between the tube and the electrosurgical knife;
    wherein the retractable means comprises a substantially semicircular hoop, and the hoop is disposed on the tube
    wherein the electrosurgical knife is disposed within the tube, and a generally L-shaped slot is provided on the internal end of the tube, and on the electrosurgical knife is disposed a stopping projection.

2. A surgical dissector as defined in claim 1, wherein the tube is connected electrically to the electro surgical knife, so as to have the functions of electrical coagulating and cuffing.

3. A surgical dissector as defined in claim 1, wherein the retractable means is affached to the tube, so that the tube can make retractable movement relative to the electro surgical knife.

4. A surgical dissector as defined in claim 1, comprising a means for rotating the tube into different angles for operation.

5. A surgical dissector as defined in claim 1, wherein in the circumferential direction of the hoop is provided with a groove, and on the tube is disposed a stopping projection.

6. A surgical dissector as defined in claim 1, wherein the head of the knife is in a shape of blade, the remaining part of the knife is tubular in shape.

7. A surgical dissector as defined in claim 1, wherein the tube is made of metal or plastics.

8. A surgical dissector as defined in claim 1, wherein the electrosurgical knife is disposed outside of the tube.

9. A surgical dissector as defined in claim 1, wherein the retractable means is attached to the electrosurgical knife.

10. A surgical dissector as defined in claim 1, wherein the electrosurgical knife is in a shape of blade, and the tube forms a suction passageway.

11. A surgical dissector as defined in claim 1, wherein the tube and the electrosurgical knife are disposed side by side, and the retractable means is attached to either the tube or the electrosurgical knife.

12. A surgical dissector as defined in claim 1, wherein an insulation tube covers the periphery surface of the tube.

13. A surgical dissector as defined in claim 1, further comprising a means for rotating the electrosurgical knife into different angles for operation.

14. A surgical dissector as defined in claim 1, wherein the tube and/or the electro surgical knife is coated with a stick-proof material.

15. A surgical dissector as defined in claim 1, wherein the beveled end with the inclined plane has an inclined angle of about 45°.

* * * * *